United States Patent [19]

Ho

[11] Patent Number: 5,109,117

[45] Date of Patent: Apr. 28, 1992

[54] METHOD OF SOMATOTROPIN NATURATION USING UREA AND A SOLUBLE ORGANIC ALCOHOL

[75] Inventor: Sa Van Ho, St. Louis, Mo.

[73] Assignee: Monsanto Company, St. Louis, Mo.

[21] Appl. No.: 543,906

[22] Filed: Jun. 26, 1990

[51] Int. Cl.⁵ .......................... C07K 3/08; C07K 15/04
[52] U.S. Cl. ...................................... 530/399; 530/324; 530/344; 530/824; 530/825; 530/397
[58] Field of Search ............... 530/399, 397, 344, 324, 530/824, 825

[56] References Cited

U.S. PATENT DOCUMENTS

| | | | |
|---|---|---|---|
| 4,511,502 | 4/1985 | Builder et al. | 530/399 |
| 4,652,630 | 3/1987 | Bentle et al. | 530/344 |
| 4,694,073 | 9/1987 | Bentle et al. | 530/399 |
| 4,731,440 | 3/1988 | Bentle et al. | 530/399 |
| 5,023,323 | 6/1991 | Ho | 530/399 |

FOREIGN PATENT DOCUMENTS 168298 7/1989 Japan.

*Primary Examiner*—Howard E. Schain
*Attorney, Agent, or Firm*—Wayne R. Eberhardt

[57] ABSTRACT

A method for the solubilization and naturation of somatotropin from refractile bodies produced by r-DNA technology wherein the refractile bodies are dissolved in an aqueous solution comprising a chaotropic agent such as urea or guanidine hydrochloride and a soluble organic alcohol such as isopropanol or benzyl alcohol. The solubilized protein is exposed to mild oxidation for a time sufficient to allow the protein to form disulfide bonds and refold to its native conformation. The presence of the alcohol suppresses the formation of somatotropin dimers and aggregates and results in higher yields of the desirable monomeric form of the protein.

15 Claims, No Drawings

METHOD OF SOMATOTROPIN NATURATION USING UREA AND A SOLUBLE ORGANIC ALCOHOL

FIELD OF INVENTION

This invention relates to the recovery of somatotropin protein produced by recombinant DNA technology, and more particularly, to an improved process for the solubilization and naturation of such proteins.

BACKGROUND OF THE INVENTION

Recombinant DNA technology has permitted the expression of heterologous protein in host cells such as E. coli bacteria. In the case of the growth hormone somatotropin, the protein is sequestered in refractile bodies within the cytoplasm of the host cells. The refractile bodies may be recovered from the host cell culture by disrupting the cell so as to release the refractile bodies, and thereupon collecting the refractile bodies as a solid pellet by differential centrifugation. The refractile bodies are solubilized in an aqueous solution of a suitable chaotropic agent such as urea or guanidine hydrochloride at an alkaline pH, generally in the range of 9-12. The solubilized proteins are subsequently naturized by contact with a mild oxidizing agent to form intramolecular disulfide bonds while refolding the protein to its biologically active native conformation. Methods for the solubilization and the naturation of somatotropin protein produced by E. coli bacteria using recombinant DNA technology are described in U.S. Pat. No. 4,511,502 and U.S. Pat. No. 4,652,630, each of which is incorporated herein by reference.

The monomeric form of somatotropin is the most biologically active, and the major yield loss occurring during the solubilization and naturation process is due to the formation of dimer and higher aggregate forms of the protein which are largely removed during further processing and purification of the monomer. Reducing the initial formation of these impurities would not only improve initial monomer yields but also reduce subsequent product losses during the monomer recovery and purification steps.

It is accordingly an object of the present invention to provide an improved process for the solubilization and naturation of somatotropin. It is a further object of the invention to provide an improved process resulting in higher yields of somatotropin monomer during the solubilization and naturation phase of the process. It is a further object of this invention to provide an improved process to reduce the formation of dimer and aggregate forms of somatotropin during the solubilization and naturation thereof. It is a still further object of this invention to improve yields of somatotropin monomer recovered from refractile bodies produced by recombinant DNA technology. These and other objects of the present invention will be apparent from the ensuing description and claims.

SUMMARY

The present invention provides a method for recovering monomeric somatotropin in high yield from refractile bodies obtained through recombinant DNA technology. Briefly stated, the process of the present invention includes the solubilization and naturation of the refractile bodies in an aqueous solution comprising a chaotropic agent such as urea or guanidine hydrochloride, and an organic alcohol such as methanol, ethanol, propanol, butanol, pentanol or benzyl alcohol.

The pH of the solution, usually above 9, and the concentration of the chaotropic agent are selected to effectively achieve solubilization of the somatotropin. The naturation of the solubilized somatotropin is achieved by contacting the solution of solubilized somatotropin with a mild oxidizing agent such as air for a time sufficient to result in the formation of the disulfide bonds present in the native confirmation of the protein and under conditions which permit the somatotropin to "refold" or assume the overall conformational shape of the native protein. Surprisingly, it has been discovered that an organic alcohol present in an amount of from about 1 to 10% by volume is effective to inhibit the formation of dimer and aggregate forms of somatotropin during the solubilization and naturation process, resulting in substantially higher yields of the desired monomer. The reduced level of impurities simplifies subsequent monomer purification and recovery with concomitantly higher process yields.

DESCRIPTION OF INVENTION

For purposes of the present invention, the following terms to have the definitions listed blow.

The term "somatotropin" is meant to include, but not be limited to, mammalian somatotropins such as human, bovine, porcine and ovine somatotropin, and others such as avian somatotropin. Somatotropin produced by recombinant DNA technology in which somatotropin is expressed by genetically transformed bacterial cells may have an amino acid sequence identical to a naturally occurring somatotropin, or may comprise variants in which amino acid residues are either added to, subtracted from or different than the amino acid sequence of the naturally occurring material, provided that such additions, deletions or substitutions in the amino acid sequence do not destroy the bioactivity of the somatotropin. Also included are the somatotropins which are associated with anions or cations, particularly salts or complexes with metal ions. Examples of suitable monovalent metal ions include sodium and potassium while examples of suitable polyvalent metal ions include zinc, iron, calcium, bismuth, barium, magnesium, manganese, aluminum, copper, cobalt, nickel and cadmium. Suitable anions include bicarbonate, acetate, glycine and borate.

"Heterologous" proteins are proteins which are normally not produced by the host cell. Recombinant DNA technology has permitted the expression of relatively large amounts of heterologous proteins such as somatotropin from transformed host cells such as E. coli. These proteins are often sequestered in insoluble refractile bodies in the cytoplasm of the host cell.

By "refractile bodies" is meant the inclusion bodies or cytoplasmic aggregates containing, at least in part, the heterologous protein to be recovered. These aggregates appear as bright spots under a phase contrast microscope.

By "host cell" is meant a microbial cell such as bacteria and yeast or other suitable cell including animal and plant cells which has been transformed to express the heterologous protein. Host cells which are contemplated by the present invention are those in which heterologous somatotropin expressed by the cell is sequestered in refractile bodies. An exemplary host cell is E. coli K12, strain W3110G [pBGHI], which has been transformed to permit expression of bovine or porcine somatotropin.

"Naturation" refers to the folding and oxidation of the heterologous somatotropin protein to its native conformation to ensure biological activity.

"Folding" refers to the return of the overall conformational shape of the protein to that of the native protein. Folding is accomplished when the amino acid sequence of the protein is free to interact and assume its native secondary and tertiary structure.

"Oxidation" refers to the formation of the intramolecular disulfide bonds in the folded protein to stabilize the native conformation and ensure biological activity.

"Refold Solution" refers to the stock solution obtained as a result of the folding and oxidation in the naturation step.

"Chaotropic Agent" refers to compounds such as guanidine hydrochloride, sodium thiocyanate, urea and various detergents which disrupt the noncovalent intermolecular bonding within the protein, permitting the amino acid chain to assume a random conformational structure.

For purposes of the present invention, refractile bodies can be recovered using standard techniques as described for example in U.S. Pat. No. 4,652,630. For example, the host cell can be disrupted by mechanical means such as a Manton-Gaulin homogenizer or French press. It is preferred that the disruption process be conducted so that cellular debris from the host organism is so disrupted that it fails to sediment from the homogenate solution under low speed centrifugation sufficient to sediment the refractile bodies. The refractile bodies are preferably resuspended, washed and centrifuged again. The supernatant is discarded yielding a substantially pure preparation of refractile bodies. Although not critical to the practice of the present invention, it is preferred that the refractile body preparation be homogenized again to ensure a freely dispersed preparation devoid of agglomerated refractile bodies. The preparation may be homogenized in a Manton-Gaulin homogenizer at 3000-5000 psig.

It is known that somatotropin proteins can be efficiently solubilized from refractile bodies of the host cell by subjecting the refractile bodies to an effective amount and concentration of urea, a weak chaotropic agent, at an alkaline pH. The concentration and absolute amount of urea needed will depend on the pH of the solution and on the amount and kind of somatotropin to be solubilized. Alternatively, the refractile bodies may be solubilized in a strong chaotropic agent such as guanidine hydrochloride. The use of urea is economically favored since it is readily available, relatively inexpensive, ecologically safer than stronger chaotropic agents and does not substantially interfere with the downstream purification procedures.

In the case of the solubilization and naturation process as described in U.S. Pat. No. 4,652,630, the protein related components of a typical refold solution generally consist of from about 30-60% somatotropin monomers, from about 10-30% somatotropin dimer and aggregates and from about 20-50% residues derived from the E. coli bacteria, including but not limited to, proteins, membrane fragments, color bodies, endotoxins, pyrogens and nucleic acids. In addition, the refold solution may contain urea at a concentration of from about 1.5 to 6M depending on the type of somatotropin being oxidized. As disclosed in U.S. Pat. No. 4,652,630, a urea concentration of between about 4 and 5M is preferred for naturation of bovine somatotropin, while a concentration of between about 2.5 and 3.5M is preferred for porcine somatotropin.

In the practice of the present invention, the general procedure for solubilization and naturation of somatotropin as described in U.S. Pat. No. 4,652,630 is followed except that an organic alcohol is added to the solution of urea or other chaotropic agent during the solubilization and/or naturation steps. The organic alcohol may be any water soluble straight chain or branched aliphatic alcohol of 1 to about 6 carbon atoms, or an aryl alcohol such as benzyl alcohol. Preferably, the alcohol is incorporated into the solution at the beginning of the solubilization process so that the benefits thereof may be obtained during the entire solubilization and naturation process. The thus preferred process is illustrated by the following examples using urea as the chaotropic agent. The method of the present invention was demonstrated with several alcohols at different concentrations and with the following three somatotropin proteins produced by recombinant DNA technology and recovered as an inclusion body suspension following homogenation and centrifugation as described above.

N-methionyl bovine somatotropin (MBST)
N-alanyl bovine somatotropin (ABST)
N-alanyl porcine somatotropin (PST)

All proportions in the following examples are by weight unless otherwise stated.

EXAMPLE 1

A 3M urea solution was prepared by adding 40 liters of 7.5M urea to 53 liters chilled water and 5 liters isopropanol (IPA). The pH of the solution was adjusted to 11.2-11.4 by the addition of 2.5M NaOH. To this solution was added 1.8 kg PST refractile body suspension which dissolve rapidly to provide 3 g/L PST in solution. The solution was stirred rapidly but without entraining air for several days to permit oxidation to occur while sampling periodically to assay for percent oxidation of PST. Upon completion of the oxidation, the concentration of oxidized monomer relative to total somatotropin was determined by Reverse Phase Chromatography (RPC) to establish refold efficiency.

The solubilization and oxidation process was repeated substituting water for the isopropanol as a control. The results of these tests were as follows:

5%(vol) IPA—81% Refold Efficiency
Control—73%

EXAMPLE 2

The method of Example 1 was repeated using concentrations of IPA from 1% to 5% by volume. Refold efficiencies were generally less than that experienced in Example 1 but indicated that at least 2% by volume IPA is required to achieve optimum refold efficiencies.

| IPA, % (vol) | 0 | 1 | 2 | 3 | 4 | 5 |
|---|---|---|---|---|---|---|
| Refold Efficiency, % | 56 | 53 | 60 | 65 | 58 | 63 |

EXAMPLE 3

The method of Example 2 was repeated substituting benzyl alcohol for isopropanol with the following results:

| BzOH, % (vol)       | 0  | 1  | 2  | 3  | 5    |
|---------------------|----|----|----|----|------|
| Refold Efficiency, % | 85 | 93 | 88 | 62 | <10 |

As indicated by the above data, optimum results are obtained at about 1% (vol) BzOH. Higher levels of BzOH have a negative effect on refold efficiency, probably as a consequence of the alcohol interfering with the ability of the protein to refold into its native conformation.

EXAMPLE 4

A series of runs were made on a 100 ml laboratory scale following the general procedure of Example 1 to determine the effect of IPA on refold efficiencies of PST, ABST and MBST at protein concentrations of 10 g/liter. The urea concentration was 3M for PST and 4.5M for the two BST runs. The following results were obtained:

| Somatotropin | IPA, % (vol) | Refold Efficiency, % |
|--------------|--------------|----------------------|
| PST          | 0            | 40–45                |
|              | 5–10         | 72                   |
| ABST         | 0            | 58                   |
|              | 5            | 75                   |
| MBST         | 0            | 70                   |
|              | 2–10         | 75–80                |

EXAMPLE 5

A series of runs were made following the general procedure of Example 4 to determine the effect of different concentrations of iso-amyl alcohol (IAA) (isopentanol) on the solubilization and naturation of PST in 3M urea at pH 11.4 with the following results:

| IAA, % (vol)         | 0  | 1  | 2  | 3  | 4  | 5  |
|----------------------|----|----|----|----|----|----|
| Refold Efficiency, % | 31 | 68 | 75 | 64 | 41 | 17 |

The above data show an optimum alcohol level at 2% by volume, and a serious decline in refold efficiency as the alcohol level is increased above 3%. This effect was also seen in Example 3 for benzyl alcohol.

EXAMPLE 6

A series of runs were made following the general method of Example 4 to determine the effect of the various butanol isomers on the solubilization and naturation of PST in 3M urea at pH 11.2–11.4 with the following results:

|            | PST Refold Efficiency, % | | | |
|------------|-----|------|------|------|
| Butanol    | n-  | iso- | sec- | ter- |
| 0, % (vol) | 31  | 28   | 31   | 27   |
| 1          | 61  | 55   | 48   | 33   |
| 2          | 68  | 71   | 59   | 46   |
| 3          | 73  | 63   | 66   | 54   |
| 4          | 69  | 64   | 68   | 60   |
| 5          | 66  | 56   | 71   | 65   |
| 10         | 10  | 24   | 65   | 75   |

From the above data, it is concluded that the primary alcohols are more effective than the secondary or tertiary alcohols, and that the optimum concentration for n-Butanol is about 3% by volume while the optimum concentration for the less effective tertiary alcohol is at least 10% by volume. These data, together with those of Example 3 and 5, indicate that an optimum concentration probably exists for all alcohols, but is seen more dramatically and at lower concentrations for those alcohols having more than 3 or 4 carbon atoms which are more effective in the method of the present invention.

EXAMPLE 7

A series of runs were made following the general method of Example 4 to determine the effect of increasing concentrations of IPA on the solubilization and naturation of MBST at 4.5M urea, pH 11.2 with the following results:

| IPA, % (vol)         | 0  | 1  | 2  | 5  | 10 |
|----------------------|----|----|----|----|----|
| Refold Efficiency, % | 75 | 83 | 85 | 88 | 86 |

The above data indicate that at least 1% IPA is desirable to enhance refold efficiency, but that up to 10% or more may be employed with good results. Isopropanol does not show an optimum concentration between 2% and 10% by volume in the solubilization and naturation of MBST.

EXAMPLE 8

A series of runs were made following the general procedure of Example 4 to determine the effect of different alcohols on the refold efficiency of PST in 3M urea at pH 11.2 with the following results:

| Alcohol           | % (vol) | Refold Efficiency, % |
|-------------------|---------|----------------------|
| none              | 0       | 41                   |
| methanol          | 5       | 58                   |
| ethanol           | 5       | 67                   |
| isopropanol       | 5       | 71                   |
| isopropanol       | 10      | 72                   |
| n-butanol         | 5       | 65                   |
| isobutanol        | 5       | 69                   |
| 3-methyl-1-butanol| 5       | 19                   |
| benzyl alcohol    | 1       | 72                   |
| benzyl alcohol    | 2       | 56                   |

From the above Examples, it is concluded that refold efficiency of somatotropin can be significantly enhanced by the addition of certain organic alcohols to the refold solution, and that the kind of alcohol and its concentration are important considerations in obtaining optimum results. While not wishing to be bound by theory, it is believed that increasing the hydrophobicity of the aqueous refold solution by adding a soluble alcohol as a co-solvent encourages the disassociation of hydrophobicly associated aggregates of somatotropin upon solution of the refractile bodies as well as minimizing the formation of aggregates during the oxidation step, but that increasing the hydrophobicity beyond an optimum level reduces refold efficiency probably as a result of the protein losing its native conformation. Larger alcohols such as isopropanol tend to be more effective than smaller ones such as methanol at concentrations of 5–10% by volume, while yet larger alcohols such as benzyl alcohol, 3-methyl-1-butanol and isopentanol must be used at lower concentrations, i.e., 3% or less to obtain optimum results.

The above Examples illustrate the discovery of the present invention that adding an organic alcohol to an aqueous solution of a chaotropic agent used for solubilization and naturation of somatotropin results in a significant increase in the amount of correctly folded, oxidized monomeric form of the somatotropin. The beneficial effect of the organic alcohol is greater at higher protein concentrations (e.g., 10 g/L) where the formation of dimers and aggregates is more of a problem than at lower protein concentrations (e.g., 3 g/L).

While the above Examples were directed to three somatotropin variants and the use of urea as the chaotropic agent, the invention is not so limited. As discussed above, chaotropic agents other than urea are known to be useful in the solubilization and naturation of somatotropins, and somatotropin variants other than PST, ABST and MBST are known to be useful and effective growth promoters. All these and other variations of the present invention which will be readily apparent to those skilled in the art are included herein.

I claim:

1. In a method for the solubilization and naturation of somatotropin protein from refractile bodies of a host cell containing said protein which comprises contacting said bodies with an aqueous solution of urea at a concentration and pH effective to achieve solubilization and thereafter contacting said solubilized protein with a mild oxidizing agent for a time sufficient to accomplish folding and oxidation of said protein, the improvement comprising including in said aqueous solution of urea a soluble organic alcohol in an amount effective to increase the relative concentration of the folded and oxidized monomeric form of said somatotropin and decrease the relative concentration of dimer and aggregate forms thereof.

2. The method of claim 1 wherein said alcohol is a straight chain or branched aliphatic alcohol of from 1 to about 6 carbon atoms.

3. The method of claim 2 wherein said alcohol is selected from the group consisting of methanol, ethanol, isopropanol, n-butanol, isobutanol, sec-butanol and ter-butanol.

4. The method of claim 3 wherein said alcohol is present in an amount of from about 1 to 10% by volume.

5. The method of claim 2 wherein said alcohol is isopentanol.

6. The method of claim 5 wherein said alcohol is present in an amount of from about 1 to 3% by volume.

7. The method of claim 1 wherein said alcohol is an aryl alcohol.

8. The method of claim 7 wherein said alcohol is benzyl alcohol.

9. The method of claim 8 wherein said alcohol is present in an amount of less than about 2% by volume.

10. The method of claim 1 wherein said somatotropin is bovine or porcine.

11. The method of claim 10 wherein the concentration of said urea is from about 1 to 8M and the pH of said solution is above about 9.

12. The method of claim 11 wherein said organic alcohol is isopropanol.

13. The method of claim 11 wherein the somatotropin is porcine and the concentration of said urea is from about 2.5 to 3.5M.

14. The method of claim 11 wherein the somatotropin is bovine and the concentration of said urea is from about 4 to 5M.

15. The method of claim 1 wherein said somatotropin protein is present in said aqueous solution at a concentration of from about 3 to 10 g/L.

* * * * *